US00PP15462P2

(12) United States Plant Patent
Jorna

(10) Patent No.: US PP15,462 P2
(45) Date of Patent: Jan. 4, 2005

(54) ***IMPATIENS* PLANT NAMED 'TAMAR PURPLE BICOLOR'**

(50) Latin Name: *Impatiens hawkeri*
Varietal Denomination: Tamar Purple Bicolor

(75) Inventor: Anita Jorna, Maasland (NL)

(73) Assignee: Fides Goldstock Breeding B.V., DeLier (NL)

( * ) Notice: Subject to any disclaimer, the term of this patent is extended or adjusted under 35 U.S.C. 154(b) by 216 days.

(21) Appl. No.: 10/698,695

(22) Filed: Oct. 31, 2003

(51) Int. Cl.[7] ..... A01H 5/00
(52) U.S. Cl. ..... Plt./318
(58) Field of Search ..... Plt./318

*Primary Examiner*—Kent Bell
(74) *Attorney, Agent, or Firm*—Mark P. Bourgeois

(57) ABSTRACT

A new cultivar of *Impatiens* plant named 'Tamar Purple Bicolor' that is characterized by a large quantity of flowers, flowers that have a large size and red-purple flowers with a dark central band. In combination, these traits set 'Tamar Purple Bicolor' apart from all other existing varieties of *Impatiens* known to the inventor.

1 Drawing Sheet

Botanical classification: *Impatiens hawkeri.*
Variety denomination: 'Tamar Purple Bicolor'.

BACKGROUND OF THE INVENTION

The present invention relates to a new and distinct cultivar of New Guinea *Impatiens* plant botanically known as *Impatiens hawkeri* and hereinafter referred to by the cultivar name 'Tamar Purple Bicolor'.

The new cultivar is the product of a breeding program conducted by the inventor in a cultivated area of De Lier, The Netherlands. The objective of the breeding program is to develop new *Impatiens* cultivars with interesting and unique flower and foliage colors.

'Tamar Purple Bicolor' is a hybrid that originated from the induced hybridization of the female or seed parent *Impatiens* 'Tamar Candy Cane' (U.S. Plant Pat. No. 12,344) and the male or pollen parent *Impatiens* 'Alexis' (not patented). The cultivar 'Tamar Purple Bicolor' was selected by the inventor in 2000 as a single plant within the progeny of the stated cross in a controlled environment of De Lier, The Netherlands.

Asexual reproduction by terminal cuttings of the new cultivar 'Tamar Purple Bicolor' were taken in 2000 in De Lier, The Netherlands by the inventor. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Impatiens* cultivar 'Tamar Purple Bicolor'. These traits in combination distinguish 'Tamar Purple Bicolor' as a new and distinct cultivar apart from all other existing varieties of *Impatiens* known to the inventor.

1. *Impatiens* 'Tamar Purple Bicolor' exhibits red-purple flowers with a dark central band.
2. *Impatiens* 'Tamar Purple Bicolor' exhibits large flowers.
3. *Impatiens* 'Tamar Purple Bicolor' exhibits a large quantity of flowers per plant.

The new cultivar 'Tamar Purple Bicolor' is distinguishable from the female parent *Impatiens* 'Tamar Candy Cane' by the following characteristics:

1. 'Tamar Purple Bicolor' has larger flowers than 'Tamar Candy Cane'.
2. 'Tamar Purple Bicolor' flowers later than 'Tamar Candy Cane'.
3. 'Tamar Purple Bicolor' has darker red-purple flowers with a dark central band.

The new cultivar 'Tamar Purple Bicolor' is distinguishable from the male parent *Impatiens* 'Alexis' by the following characteristics:

1. 'Tamar Purple Bicolor' has more flowers than 'Alexis'.
2. 'Tamar Purple Bicolor' flowers earlier than 'Alexis'.
3. 'Tamar Purple Bicolor' has red-purple flowers with a dark central band.

BRIEF DESCRIPTION OF THE DRAWING

The accompanying photograph illustrates the distinguishing traits of *Impatiens* 'Tamar Purple Bicolor'. The plant in the photograph shows an overall view of a 10 week old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Impatiens* cultivar named 'Tamar Purple Bicolor'. Data was collected in De Lier, The Netherlands from 10 week glass greenhouse grown plants in 12 cm diameter containers. The time of year was June and the temperature was kept at 20° Centigrade during the day and night. The light level was natural outdoor light and there were no photoperiodic treatments or growth retardants used. Color determinations are in accordance with The Royal Horticultural Society Colour Chart 2001 edition, except where general color terms of ordinary dictionary significance are used. The growing requirements are similar to the species. 'Tamar Purple Bicolor' has not been tested under all possible conditions and phenotypic differences may be observed with variations in environmental, climatic, and cultural conditions, however, without any variance in genotype.

Botanical classification: *Impatiens* 'Tamar Purple Bicolor'.
Use: Ornamental.
Parentage: 'Tamar Purple Bicolor' is a hybrid plant that resulted from the induced hybridization of the following parent plants:
*Female parent.*—*Impatiens* 'Tamar Candy Cane'.
*Male parent.*—*Impatiens* 'Alexis'.
Vigor: Moderate.
Growth rate: Approximately 7 cm. per month.
Growth habit: Broad Upright.
Plant shape: Rounded.
Suitable container size: 12 cm container.
Height: 26 cm. in height.
Width: 39 cm. in width.
Hardiness: USDA Zone 10.
Propagation: Terminal cuttings.
Time to initiate roots: Approximately 5–8 days to produce roots on an initial cutting.
Time to produce a rooted cutting or liner: Approximately 14–21 days.
Crop time: From a rooted cutting, approximately 9 weeks are required to produce a finished flowering plant.
Root system: Fine and fibrous.
Stem:
*Branching habit.*—Basal branching and lateral branches.
*Average number of lateral branches.*—6.
*Pinching.*—Yes.
*Lateral branch diameter.*—1 cm. in diameter.
*Lateral branch length.*—19 cm. in length.
*Lateral branch strength.*—Moderately strong.
*Stem color.*—184 A.
*Pubescence.*—Absent.
*Internode length.*—6.2 cm. between nodes.
*Shape.*—Round.
*Surface.*—Glabrous, slightly glossy.
Foliage:
*Texture.*—Both sides smooth and glossy.
*Leaf arrangement.*—Whorled, 5 per whorl.
*Compound or single.*—Single.
*Quantity of leaves per lateral branch.*—20.
*Leaf shape.*—Elliptic.
*Leaf apex.*—Acute.
*Leaf base.*—Attenuate.
*Leaf length.*—12 cm. in length.
*Leaf width.*—4.2 cm. in width.
*Pubescence.*—Absent.
*Leaf margin.*—Serrate.
*Vein pattern.*—Pinnate.
*Young leaf color* (*lower surface*).—186C.
*Young leaf color* (*upper surface*).—147A.
*Mature leaf color* (*lower surface*).—148B.
*Mature leaf color* (*upper surface*).—139A.
*Vein color* (*lower surface*).—187B.
*Vein color* (*upper surface*).—187C.
*Leaf attachment.*—Petiolate.
*Petiole dimensions.*—2.0 cm. in length and 4.0 mm. in width.
*Petiole color upper side.*—183C.
*Petiole color lower side.*—187B.
Flower:
*Flower arrangement.*—Solitary, axillary flowers.
*Inflorescence type.*—Solitary.
*Flowering habit.*—Continuous.
*Quantity of flower per lateral stem.*—Approximately 20.
*Quantity of flowers buds per lateral stem.*—Approximately 20.
*Quantity of flowers and buds per plant.*—Approximately 240.
*Flowering season.*—Late spring to autumn.
*Rate of flower opening.*—Approximately 10% of the flowers are opened at once.
*Fragrance.*—None.
*Flower bud length.*—1.2 cm. in length.
*Flower bud diameter.*—7 mm. in diameter.
*Flower bud shape.*—Ovate.
*Bud color.*—187B.
*Rate of bud opening.*—5 days.
*Flower aspect.*—Outward.
*Flower shape.*—Irregular, flowers somewhat cupped and rounded rectangular in shape.
*Flower dimensions.*–5.4 cm. in diameter and 2 cm. in height.
*Flower longevity.*—Lasts approximately 10 days on plant.
*Petal appearance.*—Dull.
*Petal texture.*—Glabrous.
*Petal arrangement.*—Irregular.
*Number of petals.*—Five in number.
*Petals fused or unfused.*—Unfused.
*Petal shape.*—Banner petal: Reniform, lateral petals: Obcordate.
*Petal margin.*—Entire.
*Petal apex.*—Banner petal: Acute, lateral petal: emarginate.
*Petal dimensions.*—Banner petal: 2.4 cm. In length, 3.5 cm. in width, lateral petal: 2.6 cm. in length and 3.4 cm. in width.
*Banner petal color when opening* (*upper side*).—Red-purple 57A, lighter at margins 65B.
*Lateral petal color when opening* (*upper side*).—Red-purple 65B, with a dark, central band 57A.
*Banner petal color when opening* (*under side*).—Gray-purple 187B, lighter at margins 58B.
*Lateral petal color when opening* (*under side*).—Red-purple 57C, with a dark, central band of 57A.
*Banner petal color fully open* (*upper side*).—Red-purple 57A, lighter at margins 65B.
*Lateral petal color fully open* (*upper side*).—Red-purple 65D, with a dark, central band 57A.
*Banner petal color fully open* (*under side*).—Red-purple 57B, darker in the center 185A.
*Lateral petal color fully open* (*under side*).—Red-purple 57C.
*Petaloids.*—Absent.
Self-cleaning or persistent: Self-cleaning.
Spur length: About 4.5 cm.
Spur texture: Smooth.
Spur color: 62D.
Sepals:
*Sepal arrangement.*—One spurred sepal located between two side sepals.
*Sepal color immature* (*upper side*).—185B.
*Sepal color immature* (*under side*).—187B.
*Sepal color mature* (*upper side*).—Spurred sepal 62D, side sepals 148D.

*Sepal color mature* (*under side*).—Spurred sepal 62D with darker central band 63A, side sepals 148D.
*Sepal surface.*—Dull and pubescent.
*Number of sepals.*—Three.
*Sepal shape.*—Ovate.
*Sepal margin.*—Entire.
*Sepal apex.*—Acute.
*Sepal base.*—Cuneate.
*Sepal dimensions.*—Side sepals 1.2 cm. in length and 7 mm. in width, spurred sepal 1.4 cm in length and 1.1 cm in width.

Pedicels:
*Pedicel dimensions.*—5.1 cm. in length and 1.5 mm. in diameter.
*Pedicel angle.*—45°.
*Pedicel color.*—144A.
*Pedical strength.*—Moderate.

Reproduction organs:
*Stamen number.*—5.
*Anther shape.*—Introrse and fused into a cap over the ovary.
*Anther dimensions.*—2 mm. In length and 2 mm. in width.
*Anther color:* 182D.
*Amount of pollen.*—Low.
*Pollen color.*—158D.
*Pistil number.*—1 in number.
*Pistil dimensions.*—1 mm. in length.
*Stigma shape.*—Capitate.
*Stigma color.*—187B.
*Style.*—Not visible.
*Ovary color.*—143A.

Seed: Seed production has not been observed.

Disease resistance: Plants of the new *impatiens* have not been observed for disease resistance.

What is claimed is:

1. A new and distinct variety of *Impatiens* plant named 'Tamar Purple Bicolor' as described and illustrated.

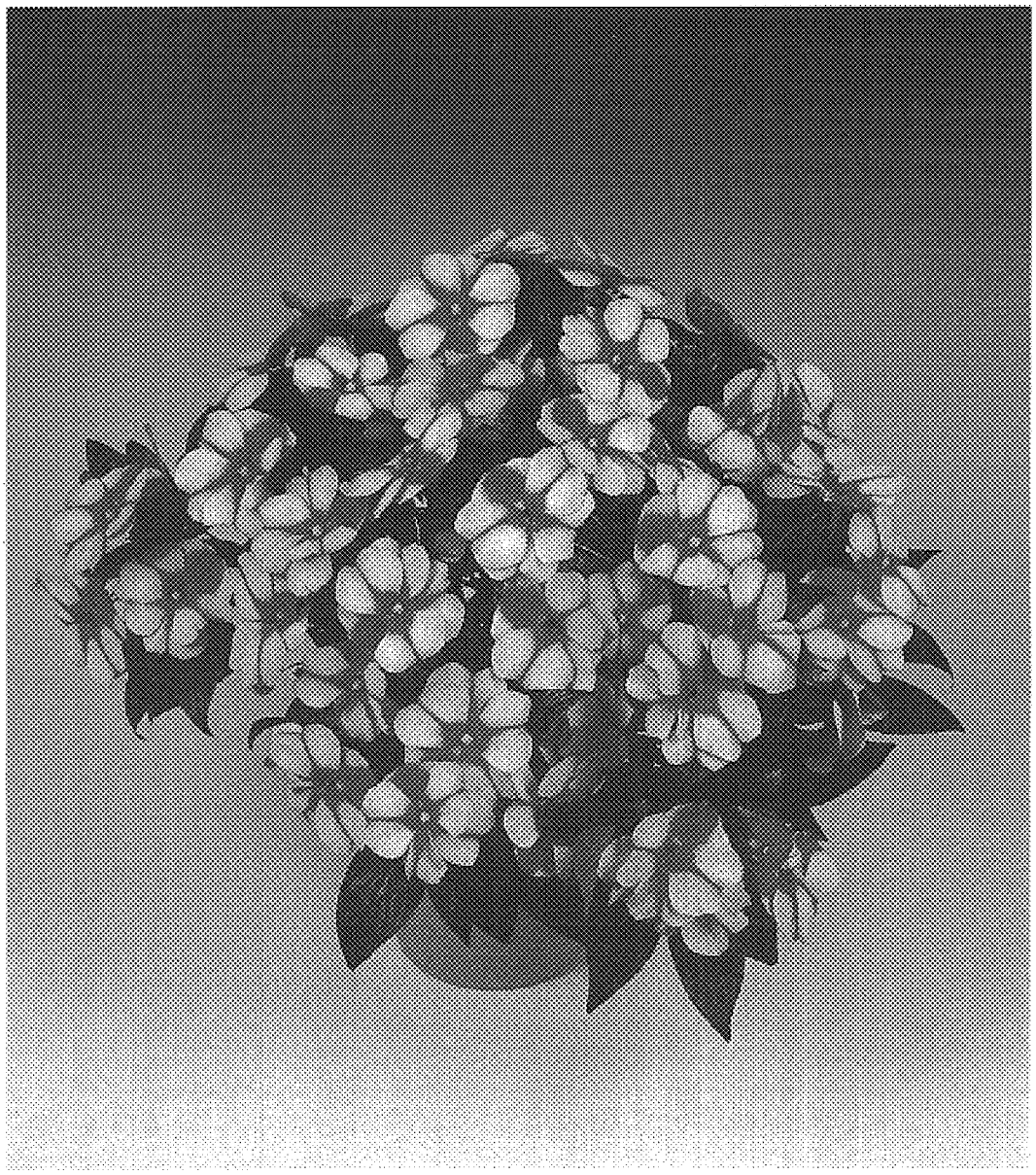

* * * * *